United States Patent [19]

Bentzen et al.

[11] 4,416,877

[45] Nov. 22, 1983

[54] ANTI-ATHEROSCLEROTIC PHARMACEUTICAL COMPOSITIONS CONTAINING DIPHOSPHONATE COMPOUNDS

[75] Inventors: Craig L. Bentzen, Chavannes de Bogis; Lan N. Mong, Nyon; Eric Niesor, Gland, all of Switzerland

[73] Assignee: Symphar S.A., Geneva, Switzerland

[21] Appl. No.: 310,314

[22] Filed: Oct. 9, 1981

Related U.S. Application Data

[63] Continuation-in-part of Ser. No. 114,423, Jan. 22, 1980, Pat. No. 4,309,364.

[30] Foreign Application Priority Data

Feb. 13, 1979 [GB] United Kingdom .................. 794992
Sep. 25, 1979 [GB] United Kingdom ................ 7933157

[51] Int. Cl.$^3$ ............................................. A61K 31/66
[52] U.S. Cl. .................................... 424/204; 260/931; 260/932
[58] Field of Search ................ 424/204; 260/931, 932

[56] References Cited

U.S. PATENT DOCUMENTS

| | | | |
|---|---|---|---|
| 2,848,475 | 8/1958 | Schmidt | 260/932 |
| 3,299,123 | 1/1967 | Fitch et al. | 260/932 |
| 3,463,835 | 8/1969 | Budnick | 260/932 |
| 4,067,971 | 1/1978 | Francis et al. | 424/204 |
| 4,113,861 | 9/1978 | Fleisch et al. | 424/204 |
| 4,137,309 | 1/1979 | Van Duzee | 424/204 |

FOREIGN PATENT DOCUMENTS

| | | | |
|---|---|---|---|
| 1394386 | 4/1964 | France | 260/932 |
| 8441M | 6/1971 | France | 260/932 |
| 777718 | 6/1957 | United Kingdom . | |
| 1026366 | 4/1966 | United Kingdom . | |

OTHER PUBLICATIONS

Pudovik et al., Index Chemicus, vol. 28; Issue 216; 1968.

Nicholson et al., *J. Org. Chem.*, vol. 36; No. 24; 1971, pp. 3843-3845.

Kosolapoff et al., Organic Phosphorus Compounds, vol. 7, Wiley Interscience, New York, 1976, pp. 267, 269 and 270.

*Primary Examiner*—Richard A. Schwartz
*Attorney, Agent, or Firm*—Young & Thompson

[57] ABSTRACT

The present invention relates to a pharmaceutical composition for increasing the relative quantity of circulating high density lipoproteins favorable augmentating the alpha/beta lipoprotein cholesterol ratios and clearing cholesterol and lipids from certain tissues and inducing hypotensive activity comprising administering to a human an effective amount of a compound of the formula:

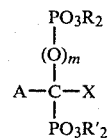

where X is H, OH, or

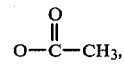

R and R' identical or different are H, $CH_3$ or $C_2H_5$; m is zero or 1; and A is selected from the group comprising $(CH_3)_3C-$, $Y-C_6H_4-$, $Y-C_6H_4-O-C(CH_3)_2-$, $Y-C_6H_4-C(CH_3)_2-$, $Y-C_6H_4-C(O)-C_6H_4-$, $Y-C_6H_4-(CH_2)_n-$ and $Y-C_6H_4-O-(CH_2)_n-$, where n is an integer from 1 to 6 and Y is H, $CH_3$, $OCH_3$, a halogen, and a pharmaceutically acceptable excipient.

12 Claims, No Drawings

ANTI-ATHEROSCLEROTIC PHARMACEUTICAL COMPOSITIONS CONTAINING DIPHOSPHONATE COMPOUNDS

The present application is a continuation-in-part of application Ser. No. 114,423, filed Jan. 22, 1980, now U.S. Pat. No. 4,309,364.

The present invention relates to a pharmaceutical composition for inducing antiatherosclerotic activity through altering the lipoprotein profile in favor of the quantity of circulating high density lipoproteins in humans and clearing cholesterol from various tissues. In addition, experimentation has also demonstrated the activity of the type of diphosphonates contained in this composition to produce hypotension by the administration of certain novel diphosphonate derivatives, and more particularly phenylalkyland phenoxylalkyldiphosphonates, hydroxydiphosphonates and phosphonophosphates.

Over the past few years, coronary heart prevention studies have been performed with common hypolipidemic agents such as clofibrate. More recently, the results of those studies have left the therapeutic effectiveness of these compounds in question (see for example New Eng. J. Med. 296, 1185–1190, 1970, Atherosclerosis Rev. 2, 113–153, 1977, The Lancet 8100, 1131–1132, 1978, and Brit. Med. J. 6152, 1585, 1978).

It is now desirable to make use of compounds which have a rapid and effective activity for decreasing cholesterol content directly in the tissues and not only in blood as it is the case for most common hypolipidemic agents.

Therefore, the present inventors have undertaken investigations on diphosphono compounds and have found that diphosphonates represented by general formula (I) possess a remarkable activity as antiatherogenic agents, as well as the ability to alter lipoprotein profiles in favor of high density lipoproteins and to directly clear cholesterol from various tissues.

This ability to remove cholesterol from tissues gives to these compounds (I) the potential of being used in diseases triggered by, or resulting from, abnormal cholesterol synthesis, metabolism and deposition. For example, cardiovascular diseases in general which are associated with cholesterol deposition in arterial walls (Atheromas), familial hypercholesterolemia and cholesterol deposition in subcutaneous tissues (Xanthomatosis) gallstones (cholesterol precipitated), cancer tissues in which cholesterol metabolism is impaired, thrombosis due to cholesterol rich-hypersensitive platelets (Shattil, S. J. et al The Journal of Clinical Investigation 55, 636–643, 1975), and diseases due to abnormal lipid content of red blood cells (Smith et al N. Engl. J. Med. 271, 396–398, 1963).

Since cholesterol is the precursor for steroid hormones (male and female sex hormones and for corticosteroids), abnormal synthesis of these hormones might be regulated by the use of such compounds. The possible uses of phosphonates in the fields described above are under investigation. Some of these compounds of formula (I) further possess an activity as hypotensive agents.

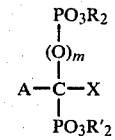
(I)

In the above formula (I), X is H, OH, or

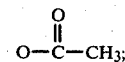

R and R' identical or different are H, $CH_3$, $C_2H_5$ or $C_4H_9$; m is zero or 1; and A is selected from the group comprising

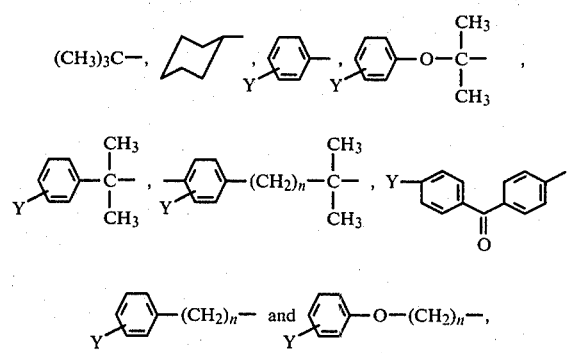

where n is an integer from 1 to 6 and Y is H, $CH_3$, $OCH_3$, or an halogen, especially as Cl or F.

The hydroxydiphosphonate compounds of formula (Ia),

where R, R' and A are as defined above, can be prepared according to the following scheme (with $R=R'=CH_3$ or $C_2H_5$):

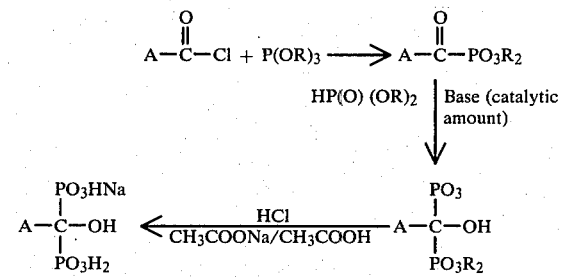

The phosphonophosphates of formula (Ib):

where R, R' and A are as defined above, can be prepared according to the following scheme (with R=R'=CH₃, C₂H₅ or C₄H₉):

$$A-\underset{\parallel}{\overset{O}{C}}-PO_3R_2 + HP(O)(OR)_2 \xrightarrow{base} A-\underset{PO_3R_2}{\overset{PO_3R_2}{\underset{|}{C}}}-H$$

The diphosphonate compounds of formula (Ic), $$A-\underset{PO_3R'_2}{\overset{PO_3R_2}{\underset{|}{C}}}-H \qquad (Ic)$$

where R, R' and A are as defined can be prepared according to the following scheme:

$$A-Z + \underset{PO_3(C_2H_5)_2}{\overset{PO_3(C_2H_5)_2}{\underset{|}{CH_2}}} \xrightarrow{NaH} A-\underset{PO_3(C_2H_5)_2}{\overset{PO_3(C_2H_5)_2}{\underset{|}{C}}}-H$$

$$\downarrow HCl$$

$$A-\underset{PO_3(CH_3)_2}{\overset{PO_3(CH_3)_2}{\underset{|}{C}}}-H \xleftarrow{HC(OCH_3)_3} A-\underset{PO_3H_2}{\overset{PO_3H_2}{\underset{|}{C}}}-H$$

where Z is Br of Cl.

The Present invention will be now further described by reference to the following Examples 1 to 10 directed to the preparation of some of the compounds of formula (I).

EXAMPLE 1

Tetramethyl 1-(p-chlorophenyl)methane 1-hydroxy 1,1-diphosphonate (Compound 4)

(Method adapted from D. A. Nicholson and H. Vaughn, Journal of Organic Chemistry 36, 3843, 1971)

Cl—(C₆H₄)—C(PO₃(CH₃)₂)(OH)(PO₃(CH₃)₂)

Dimethyl phosphite (4.40 g, 40 mmol) and di (n-butyl)amine (0.24 g, 2 mmol) were dissolved in 90 ml ether and the resulting solution was cooled to 0° C. Dimethyl p-chlorobenzoylphosphonate (9.96 g, 40 mmol) (prepared according to Journal of American Chemical Society 86, 3862, 1964) was added dropwise with rapid stirring. A white solid separated out almost immediately. The mixture was stirred for one hour at 0°, and filtration yielded 13.0 g (36 mmol) of the title compound.

Purification was done by dissolving the crude compound in acetone at room temperature and adding ether to crystallize it (acetone:ether ratio=3:1). 7.9 g (22 mmol) of white crystals were obtained, with a yield (pure compound) of 55%.

| | yield (crude) = | 90% |
|---|---|---|
| | mp = | 119–123° C. |
| IR (KBr) | 3260 cm⁻¹ | OH |
| | 2880 | aliphatic C—H |
| | 1500 | aromatic C—C |
| | 1280 + 1240 | P=O |
| | 1060 | P—O—C |
| MS:m/e = | 360 (M + 2)⁺ | 17% |
| | 358 (M)⁺ | 52% |
| | 251 (M + 2—PO₃Me₂)⁺ | 33% |
| | 249 (M—PO₃Me₂)⁺ | 100% |

NMR (CDCl₃): δ=7.90-7.20 (multiplet, 4H): phenyl group. 4.50-4.20 (triplet, 1H, J=7 Hz): H from hydroxyl group, removed through exchange with deuterium oxide. 3.90-3.50 (multiplet, 12H): H from methyl groups.

Analysis: C₁₁H₁₇ClO₇P₂; Calculated: C 36.84, H 4.78, P 17.27%; Found: C 36.81, H 4.78, P 17.26%.

As verification of its structure, compound 4 was transformed into the corresponding hydroxydiphosphonic acid, mono sodium salt (compound 10), as follows:

Cl—(C₆H₄)—C(PO₃HNa)(OH)(PO₃H₂)

A mixture of 3.59 g (10 mmol) of compound 4 and 15 g of 37% hydrochloric acid was refluxed for 3 hours. The evaporation of HCl and H₂O left 3.2 g (10 mmol) of white solid.

mp: 192°–194° C. (crude)

yield: 100% (crude)

For purification purpose, hydroxy (p-chlorophenyl) methylenediphosphonic acid was transformed into its monosodium salt, according to the following purification method adapted from P. F. Pflaumer and J. P. Filcik, Chemical Abstracts 72, 55656k, 1970:

The solid obtained as described above was dissolved in a mixture of 4.8 g (80 mmol) of acetic acid and 0.7 g (39 mmol) of water at 95°. Sodium acetatetrihyrate (1.36 g, 10 mmol) was then added gradually. A voluminous precipitate appeared almost instantly. It was filtrated and washed copiously with ether until the smell of acetic acid disappeared. The rinsed precipitate was recrystallized in an ethanol:water (20:80) mixture to give 1.94 g (6 mmol) of white powder of 1-hydroxy 1 (p-chlorophenyl)methane 1,1-diphosphonic acid, monosodium salt.

Yield: 60%

EXAMPLE 2

Tetramethyl 2,2-dimethyl 2(p-chlorophenoxy) ethane 1-hydroxy 1,1-diphosphonate (Compound 7)

(Method adapted from K. D. Berlin et al, Journal of Organic Chemistry 30, 1265, 1965, and D. A. Nicholson and H. Vaughn, Journal of Organic Chemistry 36, 3843, 1971).

Cl—(C₆H₄)—O—C(CH₃)₂—C(PO₃(CH₃)₂)(OH)(PO₃(CH₃)₂)

p-Chlorophenoxyisobutyryl chloride was first prepared by alkaline hydrolysis of ethyl p-chlorophenoxyisobutyrate and refluxing the acid obtained in thionyl chloride, in following the standard procedures.

An amount of 10.6 g (86 mmol) of trimethyl phosphite was added dropwise to 20.0 g (86 mmol) of p-chlorophenoxyisobutyryl chloride cooled to 0° C. As verification of the reaction, evolution of methyl chloride could be observed. Distillation under reduced pressure gave 19.0 g (62 mmol) of dimethyl p-chlorophenoxyisobutyrylphosphonate as an almost colorless oil.

| bp = | 115–118°/5.10$^{-2}$ Torr | |
|---|---|---|
| yield = | 72% | |
| IR (film) | 3000 cm$^{-1}$ | aliphatic C—H |
| | 1740 | C=O |
| | 1500 | aromatic C—C |
| | 1250 | P=O |
| | 1050 | P—O—C |
| | 830 | 1,4-disubstituted phenyl |

Then a solution of 2.86 g (26 mmol) dimethyl phosphite and 0.18 g (1.4 mmol) di(n-butyl)amine in 65 ml ether was cooled to 0° C., and dimethyl p-chlorophenoxyisobutyrylphosphonate (7.97 g, 26 mmol) was introduced slowly with rapid stirring. A white solid began to form almost immediately. The reaction was left to stir at 0° C. for one hour, then the solid was separated by filtration. Recrystallization in benzene:hexane (60:40) gave 7.18 g (17.2 mmol) of white feathery crystals of the title compound i.e. tetramethyl 2,2-dimethyl 2(p-chlorophenoxy) ethane 1-hydroxy 1,1-diphosphonate.

| mp = | 137–139° C. | |
|---|---|---|
| yield = | 66% | |
| IR (KBr) | 3360 cm$^{-1}$ | OH |
| | 3000 | aliphatic C—H |
| | 1500 | aromatic C—C |
| | 1250 + 1220 | P=O |
| | 1070 | P—O—C |
| | 860 | 1,4-disubstituted phenyl |

NMR (CDCl$_3$): δ=7.4–7.0 (multiplet, 4H): phenyl group 4.0–3.70 (multiplet, 12H): H from methyl groups bound to the phosphonate moieties 3.6–3.4 (hump, 1H): H from the hydroxyl group, removed through exchange with D$_2$O 1.58 (singlet, 6H): H from the branched methyl groups.

Analysis: C$_{14}$H$_{23}$ClO$_8$P$_2$; Calculated: C 40.45 H 5.58 P 14.90%; Found: C 40.29 H 5.94 P 14.93%.

EXAMPLE 3

Tetramethyl 1[4(4'-chlorobenzoyl)-phenyl]methane 1-hydroxy 1,1-diphosphonate (Compound 9)

(Method adapted from D. A. Nicholson and H. Vaughn, Journal of Organic Chemistry 36, 3843, 1971).

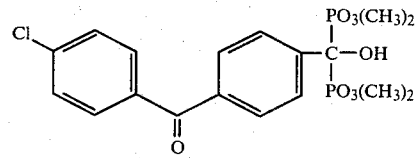

The starting compound 4(4'-chlorobenzoyl)-benzoyl chloride was prepared according to G. E. Robinson and J. M. Vernon, Journal of Chemical Society (C), 2586, 1970, and E. Wertheim, Journal of American Chemical Society 55, 2540, 1933.

Trimethyl phosphite (10.9 g, 88 mmol, 10% excess) was added dropwise to the acid chloride (22.4 g, 80 mmol) heated to just below the melting point (about 100°). The reaction was exothermic and the white crystals of acid chloride turned into a brown oil with considerable foaming. The reaction mixture was stirred at 100° for thirty minutes. Upon standing and cooling the oily material was transformed into an orange solid. Recrystallization in a 60:40 chloroform:petroleum ether mixture gave 20 g (56.7 mmol) of pure dimethyl 4(4'-chlorobenzoyl)benzoylphosphonate.

| mp = | 95–97° | |
|---|---|---|
| | | (yellow powder) |
| yield = | 71% | |
| IR (KBr) | 2960 cm$^{-1}$ | aliphatic C—H |
| | 1665 + 1650 | C=O (pertaining to the benzoylphosphonate and benzophenone moieties) |
| | 1590 | aromatic C—C |
| | 1250 + 1260 | P=O |
| | 1050 + 1030 | P—O—C |

Then a mixture of 2.20 g (20 mmol) of dimethyl phosphite and 0.144 g (1.10 mmol) di(n-butyl) amine in 40 ml ether was cooled to 0° C., and a filtered solution of 7.04 g (20 mmol) of dimethyl 4(4'-chlorobenzoyl) benzoylphosphonate in 40 ml dichloromethane was introduced dropwise. A white precipitate soon separated out of the yellow mother liquor. The reaction mixture was stirred for one hour at 0° C. and the precipitate was filtered and washed by ether. Recrystallization in acetone gave white crystals (2.4 g, 5.2 mmol) of tetramethyl 1[4(4'-chlorobenzoyl)phenyl]methane 1-hydroxy 1,1-diphosphonate.

| mp = | 150–153° C. | |
|---|---|---|
| yield = | 26% | |
| IR (KBr) | 3280 cm$^{-1}$ | OH |
| | 1670 | C=O |
| | 1600 | aromatic C—C |
| | 1260 + 1240 | P=O |
| | 1050 + 1030 | P—O—C |

NMR (CDCl$_3$): δ=8.10–7.30 (multiplet, 8H): H from the two phenyl groups 4.50–4.30 (triplet, 1H, J=7 Hz): H from hydroxyl group, removed through exchange with D$_2$O 3.95–3.60 (multiplet, 12H): H from the methyl groups Analysis: C$_{18}$H$_{21}$ClO$_8$P$_2$; Calculated: C 46.72, H 4.57, P 13.38; Found: C 46.64, H 4.59, P 13.20.

Compound 9 was transformed into the corresponding hydroxydiphosphonic acid, monosodium salt (Compound 11) by following exactly the procedure used for the synthesis of Compound 10.

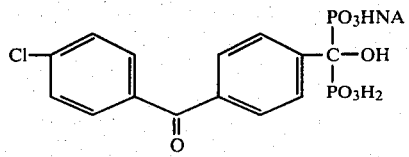

Analysis: C$_{14}$H$_{12}$ClO$_8$P$_2$Na; Calc P 14.45; Found P 10.02%.

EXAMPLE 4

Dimethyl α(dimethoxyphosphinyl) p-chlorobenzyl phosphate (Compound 16)

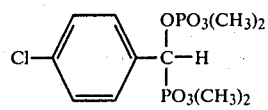

Dimethyl p-chlorobenzoylphhosphonate (9.96 g, 40 mmol) was introduced dropwise into a solution of equimolar amounts of dimethyl phosphite (4.40 g, 40 mmol) and di(n-butyl) amine (5.17 g, 40 mmol) in 90 ml ether that was cooled to 0° C. prior to the addition. A white solid began to form almost immediately. After stirring for one hour at 0° C., the solid was separated by filtration. Recrystallization performed at room temperature in a 1:3 dichloromethane: Ether mixture gave 12.0 g (33 mmol) of white crystals.

| mp | = | 81–82° | |
|---|---|---|---|
| yield | = | 82% | |
| IR (KBr) | = | 2980 cm$^{-1}$ | aliphatic C—H |
| | | 1500 | aromatic C—C |
| | | 1290 + 1260 | P=O |
| | | 1050 | P—O—C |

NMR (CDCl$_3$): δ=7.5-7.3 (multiplet, 4H): phenyl group. 5.85-5.40 (double doublet, J=11 and 13 Hz, 1H): H from the methine group, non removable through exchange with deuterium oxide. 3.95-3.50 (multiplet, 12H): H from the methyl groups.

Elementary analysis: C$_{11}$H$_{17}$ClO$_7$P$_2$; Calculated: C 36.84, H 4.78, P 17.27%; Found: C 36.71, H 4.86, P 17.33%.

The non-halogenated compound: dimethyl α(dimethoxyphosphinyl) benzylphosphate (compound 13) was prepared by the same method with the only difference that purification was carried out by means of high-vacuum distillation. A better yield (76%) was obtained with the procedure described in this patent than with the method published in the literature: lit. yield=65%, according to R. S. Davidson et al, Journal of Chemical Society (C), p. 1547 (1967).

EXAMPLE 5

Dimethyl 1-(dimethoxyphosphinyl) 2,2-dimethyl 2(p-chlorophenyl) ethylphosphate (compound 21)

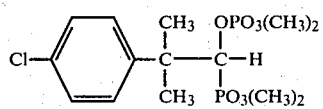

Dimethylation of p-chlorophenylacetonitrile by means of sodium amide and methyl iodide in ether gave dimethyl p-chlorophenylacetonitrile. Hydrolysis of this nitrile followed by reflux of the obtained acid in thionyl chloride yielded p-chlorophenylisobutyryl chloride.

Dimethyl p-chlorophenylisobutyrylphosphonate was prepared in 90% yield by adding an equimolar amount of trimethylphosphite to the above described acid chloride cooled to 0°.

| bp = 108–110°/5.10$^{-2}$ Torr (white oil) | | |
|---|---|---|
| IR (film) | 1690 cm$^{-1}$ | C=O |
| | 1270 | P=O |
| | 1070 + 1040 | P—O—C |

Then a solution of 3.30 g (30 mmol) of dimethylphosphite and 3.1 g (24 mmol) of di (n-butyl) amine was cooled to 0° and dimethyl p-chlorophenylisobutyrylphosphonate (8.72 g, 30 mmol) was introduced with rapid stirring. A white solid soon separated out. After stirring for one hour at 0° the solid was separated by filtration. Recrystallization in ether gave 9.0 g (75%) of white crystals of the title compound, dimethyl 1-(dimethoxyphosphinyl) 2,2-dimethyl 2(p-chlorophenyl) ethylphosphate

| mp = 62–63° | | |
|---|---|---|
| IR (KBr) = | 2980 cm$^{-1}$ | aliphatic C—H |
| | 1500 | aromatic C—C |
| | 1280 + 1260 | P=O |
| | 1080 + 1030 | P—O—C |
| MS (m/e) = | 402 (M + 2)$^+$ | 0.5% |
| | 400 (M)$^+$ | 1.5% |
| | 248 (M − Cl—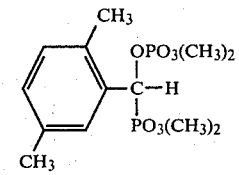− + H)$^+$ | 100% |

NMR (CDCl$_3$) δ=7.5-7.25 (multiplet, 4H): phenyl group 5.05-4.80 (double doublet, J=9 and 12 Hz, 1H): H from the methine group, non removable through exchange with D$_2$O, 3.85-3.50 (multiplet, 12H): H from the four methyl groups bound to the phosphate and phosphonate moieties, 1.58 and 1.54 (two partially overlapped singlets, 6H): H from the two branched methyl groups.

Analysis: C$_{14}$H$_{23}$ClO$_7$P$_2$; Calculated: C 41.96, H 5.79, P 15.46; Found: C 41.67, H 5.83, P 15.22.

EXAMPLE 6

Dimethyl α-(dimethoxyphosphinyl)2,5-dimethylbenzyl phosphate (compound 19)

Dimethyl 2,5-dimethylbenzoylphosphonate was prepared in 80% yield by adding an equimolar amount of trimethyl phosphite to 2,5-dimethylbenzoyl chloride.
bp=110°–112°/5.10$^{-2}$ Torr.
IR (film)=1660 (C=O), 1270 (P=O), 1040 (P-O-C)

A mixture of 5.0 g (20.7 mmol) dimethyl 2,5-dimethylbenzoylphosphonate and 2.73 g (24.8 mmol) dimethyl phosphite was heated at 110° for 5 h. The excess of dimethyl phosphite and the unreacted benzoylphosphonate were removed under vacuum. The yellow viscous residue was then purified by column chromatography with chloroform as the eluent. Dimethyl α-(dimethoxyphosphinyl)2,5-dimethylbenzyl phosphate was obtained as a white oil (2.06 g, 29%); GLC and TLC analysis showed the compound to be pure.

| IR (film) | 2980 cm$^{-1}$ | aliphatic C—H. |
|---|---|---|
|  | 1500 | aromatic C—C. |
|  | 1270 | P=O |
|  | 1040 | P—O—C |

NMR (CDCl$_3$) δ=7.45-7.05 (multiplet, 3H): phenyl group 5.95-5.70 (double doublet, J=10 and 12 Hz, 1H) H from the methine group, 3.85-3.45 (multiplet, 12H): H from the four methyl groups bound to the phosphate and phosphonate moieties 2.40-2.35 (two partially overlapped singlets, 6H): methyl groups bound to the phenyl group.

Analysis: C$_{13}$H$_{22}$O$_7$P$_2$; Calculated: C 44.33, H 6.30, P 17.59%; Found: C 43.91, H 6.63, P 17.20%.

EXAMPLE 7

Dimethyl [α-(dimethoxyphosphinyl) 4-(4'-chlorobenzoyl)]benzyl phosphate (compound 23)

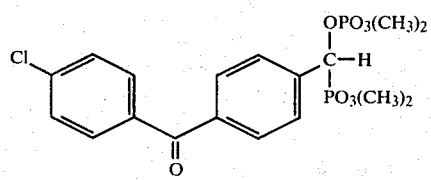

A solution of 4.90 g (10.6 mmol) of tetramethyl 1-[4(4'-chlorobenzoyl)-phenyl]methane 1-hydroxy 1,1-diphosphonate (compound 9) in 450 ml ethanol was refluxed for 6 hours. The solvent was then evaporated and the residue was recrystallized from a 1:4 dichloromethane:ether mixture. An amount of 3.9 g (79%) of white crystals of compound 23 was obtained.

| mp = 113-114° | | |
|---|---|---|
| IR (KBr) | 1660 cm$^{-1}$ | C=O |
|  | 1290 + 1270 | P=O |
|  | 1040 | P—O—C |
| MS (m/e) | 464 (M + 2)$^+$ | 15% |
|  | 462 M$^+$ | 45% |
|  | 355 (M + 2-PO$_3$Me$_2$)$^+$ | 30% |
|  | 353 (M—PO$_3$Me$_2$)$^+$ | 100% |

NMR (CDCl$_3$): δ=7.95-7.50 (multiplet, 8H): H from the two phenyl groups. 5.65 (double doublet, J=11 and 13 Hz, 1H): H from the methine group (non removable through exchange with deuterium oxide). 3.80-3.60 (multiplet, 12H): H from the methyl groups.

Analysis: C$_{18}$H$_{21}$ClO$_8$P$_2$; Calculated: C 46.72, H 4.57, P 13.38; Found: C 46.48, H 4.77, P 13.12.

EXAMPLE 8

Tetraethyl 4-phenylbutylidene 1,1-diphosphonate (Compound 29)

(Method adapted from H. R. Hays and T. J. Logan, Journal of Organic Chemistry 31, 3391, 1966, and from O. T. Quimby et al, Journal of Organometallic Chemistry 13, 199, 1968).

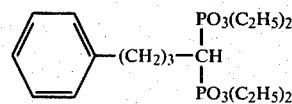

Tetraethyl methylenediphosphonate (23.06 g, 80 mmol) prepared according to Monatshefte Chemie 81, 202, 1950 was added dropwise to a dispersion of sodium hydride (1.92 g, 80 mmol) in 30 ml toluene. When the evolution of hydrogen ceased, 3-phenylpropyl bromide (19.9 g, 100 mmol) was added and the mixture was heated to 90° C. for 14 hours and then to 110° C. for 2 more hours. After removal of the toluene under vacuum, the residue was dissolved in chloroform, washed repeatedly with a saturated sodium chloride solution and freed of water by passing through a silicone-treated filtered. Distillation under reduced pressure gave a colorless oil boiling at 135°-145°/5.10$^{-2}$ Torr. A careful refractionation yielded 10.4 g (26 mmol) of tetraethyl 4-phenylbutylidene 1,1-diphosphonate.

| pb = 141-143°/5.10$^{-2}$ Torr | | |
|---|---|---|
| yield = 32% | | |
| IR (film) | see Table III | |
| MS (m/e) | 406 (M)$^+$ | 61% |
|  | 301 | 100% |
|  | 269 (M—PO$_3$Et$_2$) | 23% |

NMR (CDCl$_3$); δ=7.35-7.20: (multiplet, 5H): phenyl group, 4.35-3.90: (quintet, 8H, J=8 Hz) H from the four methylene groups attached to the phosphonate moieties, 2.80-1.70: (multiplet, 7H): H from the odd hydrogen and from the side-chain methylene groups, 1.50-1.20: (triplet, 12H, J=7 Hz: H from the four methyl groups.

Analysis: C$_{18}$H$_{32}$O$_6$P$_2$; Calculated: C 53.20, H 7.94, P 15.24; Found: C 53.08, H 8.05, P 15.02.

EXAMPLE 9

4-Phenylbutylidene 1,1-diphosphonic acid (Compound 33)

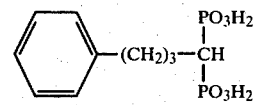

A mixture of 8.15 g (20 mmol) of tetraethyl 4-phenylbutylidene 1,1-diphosphonate and 40 g of 37% hydrochloric acid was refluxed for 15 hours. Evaporation to dryness of the clear acid solution gave a white sticky solid. The compound was repeatedly triturated with ether to remove its stickiness. Recrystallization from an ether:acetone:hexane (30:40:30) mixture gave 3.8 g (13 mmol) of white powder.

mp=190°-192° C.
yield=65%

IR (KBr): see Table III

EXAMPLE 10

Tetramethyl 4-phenylbutylidene 1,1-diphosphonate (Compound 37)

(Method adapted from D. A. Nicholson et al., Journal of Organic Chemistry 35, 3149, 1970)

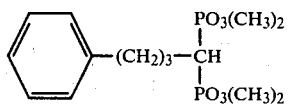

A suspension of 4.5 g (15 mmol) of 4-phenylbutylidene 1,1-diphosphonic acid and 9.8 g (92 mmol) of trimethyl orthoformate was heated to reflux for ninety minutes. Rapid stirring was necessary to assure intimate contact of the two phases. An excess of trimethyl orthoformate (9.8 g, 92 mmol) was then added and the mixture was refluxed for a further thirty minutes. The methanol and methyl formate that were formed were removed by distillation thereby allowing the reaction temperature to rise. Heating was continued until one phase remained and trimethyl orthoformate began to distil. After removal of this reagent, the brown residue was submitted to vacuum distillation to give 3.3 g (9.3 mmol) of a colorless oil.

bp=135°-138° (5.10$^{-2}$ mmHg)
yield=62%
IR (film): see Table III
NMR (CDCl$_3$): δ=7.35-7.20 (multiplet, 5H): phenyl group 3.95-3.60 (doublet, 12H, J=11 Hz): H from the methyl groups attached to the phosphonate moieties. 2.80-1.60 (multiplet, 7H): H from the odd hydrogen and from the sidechain methylene groups.

Analysis: C$_{14}$H$_{24}$O$_6$P$_2$; Calculated: C 48.03, H 6.86, P 17.69; Found: C 47.75, H 7.03, P 17.41.

Other compounds of formula (I) were prepared according to similar processes as above, and the physical properties of the compounds (I) prepared are shown on the following Tables I, II and III.

NMR spectra of the hydroxy diphosphonate ester compounds (Ia) (Compounds 1 to 9) all displayed the characteristic absorptions of a hydroxy group: a sharp peak (for compounds 1, 7 and 8), or a triplet (compounds 2, 3, 4, 5, 6, and 9) at δ~4 that all were removed through exchange with deuterium oxide.

The NMR spectra of phosphonophosphate compounds (Ib) also displayed a characteristic pattern:
- δ=7.50-7.30 multiplet, phenyl group
- δ=5.80-5.40 (Compounds 13, 14, 15, 16, 17, 18, 19, 24, and 25)
- 5.10-4.80 (Compounds 12, 20, 21, and 22) double doublet corresponding to the absorption of the odd hydrogen atom, non removable through exchange with deuterium oxide
- δ=3.90-3.50 multiplet, methyl ester groups
- δ=1.60-1.55 (only for compounds 20, 21 and 22 two singlets, branched methyl groups

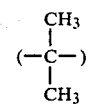

The MS spectra of all diphosphonate ester compounds (Ia–Ic) showed a characteristic pattern: a molecular ion (M+) in significant intensity (10–30%) and a base peak (100%) corresponding to the loss of a phosphonate ester group (M-PO$_3$R$_2$)+.

The sole exception is the mass spectrum of compound 7 which did not show the molecular ion but peaks corresponding to the breakdown of the molecule. The structure of the compound was established without ambiguity by elemental analysis.

TABLE I

| Physical properties of hydroxydiphosphonates of formula (Ia) | | | | |
|---|---|---|---|---|
| Compound No. | Formula (Ia) A. | R, R' | mp (°C.) | IR absorptions (cm$^{-1}$) |
| 1 | (CH$_3$)$_3$C— | CH$_3$ | 110–112 | 3250: OH |
| 2 | C$_6$H$_5$— | CH$_3$ | 129–131 | 2980 alphatic C—H |
| 3 | CH$_3$—C$_6$H$_4$— | CH$_3$ | 110–113 | |
| 4 | Cl—C$_6$H$_4$— | CH$_3$ | 119–123 | 1260 + 1240: P=O |
| 5 | F—C$_6$H$_4$— | CH$_3$ | 118–122 | 1195: P—O—CH$_3$ |
| 6 | CH$_3$O—C$_6$H$_3$(OCH$_3$)— | CH$_3$ | 120–123 | 1050: P—O—C |
| 7 | Cl—C$_6$H$_4$—O—C(CH$_3$)$_2$— | CH$_3$ | 137–138 | 3340, 1500, 1260, 1240, 1195, 1070 |

TABLE I-continued

Physical properties of hydroxydiphosphonates of formula (Ia)

| Compound No. | Formula (Ia) A | R, R' | mp (°C.) | IR absorptions (cm$^{-1}$) |
|---|---|---|---|---|
| 8 | Cl—C$_6$H$_4$—CH$_2$—C(CH$_3$)$_2$—CH$_3$— | CH$_3$ | 128–131 | |
| 9 | Cl—C$_6$H$_4$—C(O)—C$_6$H$_4$— | CH$_3$ | 150–153 | 3280, 1670 (C=O)<br>1600, 1260 + 1240<br>1050 + 1030 |
| 10 | Cl—C$_6$H$_4$— | ¾ H | >300 | 3460, 3000 (broad) P—O—H—<br>1200, 1080, 950 |
| 11 | Cl—C$_6$H$_4$—C(O)—C$_6$H$_4$— | ¾ H<br>¼ Na | >300 | 3460, 3000 (broad) P—O—H—<br>1670 (C=O) 1200–1080–950 |

TABLE II

Physical properties of phosphonophosphates of formula (Ib)

| Compound No. | Formula (Ib) A | R, R' | mp (°C.) | bp (°C./Torr) | IR absorptions (cm$^{-1}$) |
|---|---|---|---|---|---|
| 12 | cyclohexyl | CH$_3$ | | 135–140/5.10$^{-2}$ | |
| 13 | phenyl | CH$_3$ | | 152–155/5.10$^{-2}$ | |
| 14 | 2-Cl-C$_6$H$_4$— | CH$_3$ | * | | |
| 15 | 3-Cl-C$_6$H$_4$— | CH$_3$ | ** | | 2980: aliphatic C—H<br>1500: aromatic C—C<br>1290 + 1260: P=O<br>1195: P—O—CH$_3$<br>1050: P—O—C |
| 16 | 4-Cl-C$_6$H$_4$— | CH$_3$ | 81–82 | | |
| 17 | 4-F-C$_6$H$_4$— | CH$_3$ | 48–49 | | |
| 18 | 4-CH$_3$-C$_6$H$_4$— | CH$_3$ | 62–63 | | |
| 19 | 2,4-(CH$_3$)$_2$-C$_6$H$_3$— | CH$_3$ | *** | | |
| 20 | C$_6$H$_5$—C(CH$_3$)$_2$— | CH$_3$ | 47–48 | | 2980: aliphatic C—C<br>1500: aromatic C—C<br>1280 + 1260: P=O<br>1200 + 1180: —C(CH$_3$)$_2$— group |
| 21 | 4-Cl-C$_6$H$_4$—C(CH$_3$)$_2$— | CH$_3$ | 62–63 | | |

TABLE II-continued

Physical properties of phosphonophosphates of formula (Ib)

| Compound No. | Formula (Ib) A | R, R' | mp (°C.) | bp (°C./Torr) | IR absorptions (cm$^{-1}$) |
|---|---|---|---|---|---|
| 22 | Cl—C$_6$H$_4$—CH$_2$—C(CH$_3$)$_2$—CH$_3$ | CH$_3$ | 45–46 | | 1195: P—O—CH$_3$<br>1050: P—O—C |
| 23 | Cl—C$_6$H$_4$—C(=O)—C$_6$H$_4$—CH$_3$ | CH$_3$ | 113–114 | | 1660 (C=O), 1290, 1270, 1040 |
| 24 | Cl—C$_6$H$_4$— | C$_2$H$_5$ | | 175–177/5.10$^{-2}$ | 2980, 1500, 1270, 1050<br>1170: P—O—C$_2$H$_5$ |
| 25 | Cl—C$_6$H$_4$— | n-C$_4$H$_9$ | **** | | 2980, 1500, 1270, 1040 |

\* and **: C$_{11}$H$_{17}$ClO$_7$P$_2$ Calc. C 36.84 H 4.78 P 17.27  Found (Cpd 14) C 36.36 H 4.73 P 16.90  Found (Cpd 15) C 36.64 H 4.94 P 17.19
*** Correct elemental analysis, see page 16.
**** C$_{23}$H$_{41}$ClO$_7$P$_2$ Calc. C 52.42 H 7.84 P 11.76  Found C 50.96 H 7.69 P 11.00

TABLE III

Physical properties of diphosphonates of formula (Ic)

| Compound No. | Formula (Ic) A | R, R' | bp (°C./Torr) | mp (°C.) | IR absorptions (cm$^{-1}$) |
|---|---|---|---|---|---|
| 26 | C$_6$H$_5$—CH$_2$— | C$_2$H$_5$ | 135–138/5.10$^{-2}$ | | 2980: aliphatic C—H<br>1500: aromatic C—C<br>1260: P=O<br>1170: P—O—C$_2$H$_5$<br>1050: P—O—C— |
| 27 | Cl—C$_6$H$_4$—CH$_2$— | C$_2$H$_5$ | 153–156/5.10$^{-2}$ | | |
| 28 | C$_6$H$_5$—(CH$_2$)$_2$— | C$_2$H$_5$ | 137–140/5.10$^{-2}$ | | |
| 29 | C$_6$H$_5$—(CH$_2$)$_3$— | C$_2$H$_5$ | 141–143/5.10$^{-2}$ | | |
| 30 | C$_6$H$_5$—CH$_2$— | H | | 210–212 | 3400–3200 (broad): OH<br>1500: aromatic C—C<br>1230: P=O<br>1040: P—O— |
| 31 | Cl—C$_6$H$_4$—CH$_2$— | H | | 237–239 | |
| 32 | C$_6$H$_5$—(CH$_2$)$_2$— | H | | 167–170 | |
| 33 | C$_6$H$_5$—(CH$_2$)$_3$— | H | | 190–192 | |
| 34 | C$_6$H$_5$—CH$_2$— | CH$_3$ | 130–132/5.10$^{-2}$ | | 2980: aliphatic C—H<br>1500: aromatic C—C<br>1270: P=O<br>1195: P—O—CH$_3$<br>1050: P—O—C |
| 35 | Cl—C$_6$H$_4$—CH$_2$— | CH$_3$ | 141–144/5.10$^{-2}$ | | |
| 36 | C$_6$H$_5$—(CH$_2$)$_2$— | CH$_3$ | 132–135/5.10$^{-2}$ | | |
| 37 | C$_6$H$_5$—(CH$_2$)$_3$— | CH$_3$ | 135–138/5.10$^{-2}$ | | |

The present invention will be now further illustrated through the following Examples 11 to 13 concerning the pharmacological activity of the compounds of formula (I).

EXAMPLE 11

Effects of diphosphonates of formula (I) on lipid metabolism in normal rats

Method used:

Groups of 4 to 5 normal male Wistar rats, weighing about 200 g were treated with diphosphonates (200 mg/kg/day) p.o. for 4 to 21 days. Water soluble compounds were given in solution in 24 mM bicarbonate buffer. Lipid soluble compounds were given in corn oil. The rats were weighed, sacrificed by decapitation (under light ether anesthesia) after overnight fasting. Blood was collected and serum used for analysis. The following blood parameters reflecting changes in lipid metabolism are reported:

- free fatty acids measured according to W. G. Duncombe (Clin. Acta 9, 122, 1964)
- triglycerides enzymatic method (Boehringer Mannheim Kit 126 012)
- phospholipids: molybdate/vanadate reaction (Boehringer Mannheim Kit 124 974)
- β-lipoprotein cholesterol was measured after heparin, $CaCl_2$ precipitation according to M. Burstein et al. (La Presse Medicale 43, 974, 1958) and to D. Watson (Clin. Chim. Acta 5, 637, 1960).

Results obtained

With the exception of compounds 1, 2 and 3, all the diphosphonates (I) tested lowered serum free fatty acids in normal rats or in cholesterol fed rats. This activity seems to be a rather general property of these diphosphonates which possess a p-chlorophenyl moiety and shows their involvement in lipid metabolism. Similar properties have been described for several hypolipidemic agents (Hypolipidemic Agents, ed. David Kritchevsky, vol 41, Handbook of Experimental Pharmacology, Springer-Verlag, 349–408, 1975). Significant decreases in serum triglycerides were measured with compounds 2, 4, 7, 9, 12, 19, 21, and 27 and the acid form of compound 4. In several cases, compounds 2, 4, 7, 13, 16, 20, 21, 23, 29, 35, and 37, serum phospholipid was found to increase. In particular, compounds 4, 23, and 35 were found to be at least two fold the most active. Cholesterol present in the β-lipoprotein fraction (very low density lipoproteins VLDL, and low density lipoproteins LDL) decreased whereas α-lipoprotein (high density lipoproteins HDL) cholesterol increased thus leading to a favorable augmentation of the α-cholesterol/β-cholesterol ratio. Activity was observed from compounds representing the three groups of Formula I where compounds 2, 4, 5, 9, 15, 16, 17, 23, 35, and 37 were found to have highly significant activity. This effect was associated in long term therapy with a decreased liver and aorta cholesterol content.

The results described above show that these diphosphonates have the property to change lipid metabolism especially to increase the amount of lipids (mainly cholesterol) carried by α-lipoproteins and decrease the amount of lipids carried by β-lipoproteins (mainly triglycerides). Since it has been shown that the amount of HDL-cholesterol inversely correlates with the risk of cardiovascular diseases (see N. E. Miller, Lipids 13, 914–919, 1978), diphosphonates having the property to increase HDL levels might be useful in the potential treatment of atherosclerosis. The most widely used hypolipidemic agent, clofibrate was tested for comparison purposes and decreased both plasma phospholipids by 33.6% and the α/β ratio by 52.2%. The results are in agreement with those published by C. E. Day et al (Artery 5, 90–109, 1979) and by K. R. Müller and G. G. Cortesi (Artery 4, 564–577, 1978) demonstrating the diclofibrate decreases HDL cholesterol in rats. It is also important to note that the acid or salt form of compound 4 and the rather simple diphosphonate compound 1, do not have these properties. It is also important to note that diphosphonic acids do not have the property to increase HDL-cholesterol values. (See W. Hollander et al., Atherosclerosis 31, 307–325, 1978 and Mellies et al., Artery 6, 38, 1979).

EXAMPLE 12

Effects of diphosphonates of formula (I) in cholesterol fed rats

Method used:

In order to increase tissue cholesterol, especially liver, rats were fed a high fat-high cholesterol diet for 10 days to 3 months, with the following diet composition: casein 20%, butter 37%, cellulose 9.1%, dextrose 18,9%, cholesterol 4.5%, sodium cholate 1.8%, minerals 7.3%, vitamins 1%, choline 0.4%.

The rats were then fed normal food and were treated for 10 days to 3 months with different compounds (200 mg/kg/day). Serum parameters described above were measured. Liver and aorta lipids were extracted according to J. Folch et al (J. Biochem. 226, 497, 1957). Total lipids were determined by the sulfophosphovanillic reaction (see N. Zölner and K. Kirsch, Z. Ges. exp. Med. 135, 545, 1962) and cholesterol by the Liebermann-Burchard reaction or appropriate enzymatic reaction.

Results obtained:

The diet described above increased liver total lipids, especially triglycerides and cholesterol, 8 to 10 fold. Treatment with compounds 2, 4, 7, 9, 13, 16, 21, 27, and 35 decreased significantly liver total lipids and/or liver cholesterol. Same effect was measured on the aortic tissue. This shows that these particular diphosphonates tested have the property to remove tissue cholesterol. Since it is well established that cholesterol deposition is an important step in the initiation and/or development of atherosclerosis, these compounds might be useful in the prevention or treatment of atherosclerotic lesions, by preventing cholesterol deposition in tissues such as the aorta.

EXAMPLE 13

Effects of acid and salt form of diphosphonates of formula (I) in hypercalceamic rats Method used:

In recent years, simple nonaryl diphosphonic acids such as dichloromethylene diphosphonate have been shown to be effective in the hypercalceamic animal model in which they inhibit aorta and kidney calcification (see M. Potokar and M. Schmidt-Dunker, Atherosclerosis 30, 313–320, 1978). They have also been shown to prevent the vitamin D-induced rise in plasma calcium. To verify this activity the acid form of compound 4 and is monosodium salt counterpart (compound 10) were also tested by using a protol similar to the one described by Potokar (see above). Briefly, groups of 4 male Wistar rats received acid or salt form of compound 4 as 0.05% solution in drinking water corresponding to about 50 mg/kg/day. The rats were treated with the compounds for 15 days.

Results obtained:

None of the esterified forms but the acid and salt forms of compound 4 decrease serum calcium by 20 and 14% respectively. However on the contrary, the diphosphonic acids tested were not found to have any effect in altering HDL-cholesterol or alpha/beta ratios. With a similar class of diphosphonic acid tested in monkeys Hollander et.al. (Atherosclerosis 31, 307-325, 1978) found that there were no changes in HDL-cholesterol lipoprotein profiles and no antiatherosclerotic effects attributed to these acids. Some results of the above described pharmacological activity tests of diphosphonates of formula (I) according to the present invention are shown in Table IV.

TABLE IV

PHARMACOLOGICAL ACTIVITY OF DIPHOSPHONATES OF FORMULA (I)

| Compounds No. | Serum Free Fatty Acids | | Serum Triglycerides | | Serum Phospholipids | | Serum Chol. $\alpha/\beta$ | | Liver Total Lipids | Liver Chol. | Aorta Total Lipids | Aorta Chol. | Serum Calcium |
|---|---|---|---|---|---|---|---|---|---|---|---|---|---|
| | N | C.F | N | C.F | N | C.F | N | C.F | C.F | C.F | C.F | C.F | |
| 1 | NS | | +24 | | −43 | | NS | | — | — | — | — | NS |
| 2 | NS | −56 | −21 | −15 | +25 | NS | | +88 | −24 | −50 | −30 | NS | NS |
| 3 | NS | | NS | | NS | | NS | | — | — | — | — | NS |
| 4 | −48 | −67 | −24 | −21 | +43 | +21 | | +220 | −31 | −56 | −47 | NS | NS |
| 5 | — | | +27 | | — | | +64 | | — | — | — | — | — |
| 7 | +28 | −40 | −33 | NS | +26 | NS | | +27 | NS | −25 | −27 | −19 | NS |
| 9 | −38 | −52 | −16 | −17 | NS | +36 | | +51 | −25 | NS | NS | −39 | NS |
| 4 Acid | −17 | | −29 | | NS | | NS | | NS | NS | NS | NS | −20 |
| 10 | −27 | | −17 | | NS | | NS | | NS | NS | NS | NS | −14 |
| Clofibrate | NS | | +19 | | −34 | | NS | | — | NS | — | — | — |
| 12 | — | | −46 | | NS | | NS | | — | — | — | — | — |
| 13 | −21 | | +32 | | +21 | | | +25 | −18 | −51 | — | — | — |
| 14 | — | | −42 | | +22 | | +34 | | — | — | — | — | — |
| 15 | — | | −37 | | NS | | +69 | | — | — | — | — | — |
| 16 | −50 | | NS | | +26 | | +121 | +169 | −32 | −57 | −37 | −30 | NS |
| 17 | — | | NS | | NS | | +81 | | — | — | — | — | — |
| 18 | — | | −33 | | NS | | NS | | NS | — | — | — | — |
| 19 | — | | NS | | NS | | +15 | | — | — | — | — | — |
| 20 | — | | +36 | | +15 | | +25 | | — | — | — | — | — |
| 21 | — | | −38 | +28 | +16 | +24 | NS | −32 | −36 | −46 | — | — | — |
| 22 | — | | −19 | | NS | | −38 | | — | — | — | — | — |
| 23 | — | | NS | | +53 | | +55 | | — | — | — | — | — |
| 24 | — | | NS | | NS | | NS | | — | — | — | — | — |
| 25 | — | | NS | | NS | | NS | | — | — | — | — | — |
| 27 | −44 | −65 | −16 | −24 | NS | NS | | −35 | NS | NS | −60 | NS | NS |
| 29 | — | | +46 | | +17 | | +33 | | — | — | — | — | — |
| 35 | −44 | | NS | | +51 | | +75 | | NS | −19 | — | — | NS |
| 37 | — | | +42 | | +33 | | +49 | | — | — | — | — | — |

Notes:
In above Table IV, results are given as % control values. Except for serum calcium, values which differ from control values by less than 15% are considered as non significant (NS).
Serum free fatty acids, triglycerides and phospholipids were measured in normal rats (N) and rats previously fed a cholesterol diet for 10 days (C.F.)
Serum $\alpha/\beta$ cholesterol, total lipids and cholesterol of liver and aorta were determined in normal rats (N) and rats which had previously been fed on high cholesterol diet (C.F.)
Serum calcium was measured in hypercalceamic rats.

The pharmacological screening of diphosphonate derivatives of formula (I) according to the present invention has shown that said compounds possess specific properties and activities upon lipids and lipid metabolism, and that they have the potential of being used in the treatment of cardiovascular disease for the following reasons:
(1) They act on lipid metabolism in normal rats by decreasing serum free fatty acids, decreasing triglycerides and increasing phospholipids. These activities might be linked to the increased HDL lipids, especially HDL cholesterol, observed most dramatically with compounds 2, 4, 5, 9, 15, 16, 17, 23, 35, and 37.
(2) They possess the important property of decreasing and removing significantly liver and aorta lipids, especially cholesterol, in high fat high cholesterol fed rats.

Following the extensive pharmacological screening of these compounds, using over 2000 animals, those showing the most potential were then subjected to toxicity testing for further selection relative to their activity/toxicity risk profiles By way of $LD_{50}$ (Lethal Dose 50) the methyl diphosphonates were discovered to have a significant lower degree of toxicity. For example compound 16 was found to have an oral $LD_{50}$ of 3042 mg/kg while the respective ethyl derivative compound 24 $LD_{50}$ was 547 mg/kg. This represents a significant six fold difference in toxicity.

From these data it can be stated that the methyl esters of formula (I) have most activity and least toxicity and therefore have the most favorable activity/toxicity risk ratio.

In order to demonstrate the real therapeutic potential and usefulness of this class of compounds in cardiovascular diseases and especially atherosclerosis, compound 16 was taken through a series of studies including clinical trials. The essential elements of these studies will be described.

It should be noted that these diphosphonate compounds are different and novel in comparison to the classical hypolipidemic compounds as illustrated in Table V. The diphosphonate ester used for comparison was the only one to increase the alpha/beta cholesterol ratio in control rats.

Treating male and female rats with 40, 400 and 800 mg/kg of compound 16 per day for 90 days produced a sustained dose response augmentation in serum high density lipoprotein cholesterol (HDL-C or $\alpha$-cholesterol) as high as 220% above controls at high dose level (Table VI). In addition there was also an impressive dose response effect in decreasing the weight of fat tissue (Table VII).

TABLE V
COMPARISON OF CLOFIBRATE, GEMFIBROZIL, AND FENOFIBRATE TO COMPOUND 16 INDUCED AUGMENTATION OF ALPHA/BETA RATIOS IN NORMAL WISTAR RATS

|  | n | alpha/beta Cholesterol Ratio |
|---|---|---|
| Controls | 5 | 7.27 ± 0.42 |
| CPD 16 Treated | 5 | 9.69 ± 0.76* |
| Clofibrate Treated | 5 | 2.76 ± 0.40* |
| Gemfibrozil Treated | 5 | 5.33 ± 0.31* |
| Fenofibrate Treated | 5 | 1.19 ± 0.20* |

Each drug was administered at 100 mg/kg for 10 days
*p < 0.01

TABLE VI
LIPOPROTEIN CHOLESTEROL CHANGES IN NORMAL RATS TREATED WITH COMPOUND 16 FOR 90 DAYS*

| Group | Sex | α-chol mg/dl | β-chol mg/dl | α/β ratio |
|---|---|---|---|---|
| Controls | male | 55 | 8.8 | 6.25 |
|  | female | 47 | 6.8 | 6.9 |
| Cpd 16 | male | 63 | 8.3 | 7.6 |
| 40 mg/kg | female | 54 | 9.0 | 6.0 |
| Cpd 16 | male | 78 | 7.6 | 11.5 |
| 400 mg/kg | female | 68 | 5.9 | 11.5 |
| Cpd 16 | male | 128 | 11.9 | 10.7 |
| 800 mg/kg | female | 117 | 10.3 | 11.3 |

*Plasma was pooled from 5 animals of each group and analyzed.

TABLE VII
WEIGHT OF FAT TISSUE FROM RATS TREATED WITH COMPOUND 16 FOR 90 Days

|  | MALES g | FEMALES g |
|---|---|---|
| Controls | 3.50 ± 1.41 n = 8 | 1.48 ± 0.68 n = 8 |
| Cpd 16 40 mg/kg | 2.49 ± 0.94 n = 8 | 1.33 ± 0.66 n = 10 |
| Cpd 16 400 mg/kg | 1.95 ± 0.52* | 0.39 ± 0.24* |
| Cpd 16 800 mg/kg | 0.97 ± 0.30* n = 5 n = 5 | 0.48 ± 0.14* n = 5 n = 5 |

*p < 0.05

In cholesterol pre-fed rabbits treated during 4 months, compound 16 produced a similar increase in HDL-cholesterol and significantly increased the α/β ratio from 0.29 to 0.94 (Table VIII). In these types of experiments where atherosclerosis had been induced in rabbits by cholesterol feeding, the cholesterol clearing effect observed previously in rats was confirmed in that treatment with compound 16 effectively decreased the pre-established cholesterol deposits from rabbit liver and aorta tissues (Tables IX and X) which also resulted in a decreased atherosclerosis surface involvement and decreased aorta intimal thickening (Table XI).

Treating a normal male Cynomolgus monkey with one single oral dose of compound 16 (250 mg/kg) showed a remarkable ability of this diphosphonate to produce a rapid increase of 39% in α/β cholesterol levels during only 6 hours (Table XII).

Additional administration of compound 16 or 5 days to this animal resulted in maintaining the elevated α/β ratio (0.88) illustrating a similar mechanism of action as seen in rats.

It was observed simultaneously that the blood pressure of this animal also decreased dramatically during this six hours period by at least 40%. It has thus been discovered that diphosphonate compounds of Formula I also possess hypotensive activity apparently through a secondary mechanism which will be discussed separately.

To further test the long term efficacity of compound 16, normal male and female Cynomolgus monkeys were treated during 60 days (Table XIII).

TABLE VIII
CHANGES IN LIPOPROTEIN CHOLESTEROL IN CHOLESTEROL PRE-FED RABBITS TREATED WITH COMPOUND 16

|  | Total Cholesterol | α-chol | β-chol | α/β-ratio |
|---|---|---|---|---|
| Controls n = 4 | 156.0 ± 74.0 | 27.2 ± 3.7 | 110.6 ± 44.2 | 0.29 ± 0.10 |
| Cpd 16 Treated n = 5 200 mg/kg per day | 127.0 ± 68.0 | 41.1 ± 11.1 | 63.4 ± 43.0 | 0.94 ± 0.20* |

Animals were fed a cholesterol rich diet for 8 weeks before treatment was started which continued for 4 months without cholesterol supplement.
*p < 0.05

TABLE IX
LIVER CHOLESTEROL CLEARING ACTIVITY OF COMPOUND 16 IN CHOLESTEROL PRE-FED RABBITS TREATED FOR 4 MONTHS

|  | n | Total Lipids mg/g | Cholesterol mg/g | Phospholipids mg/g | Cholesterol Free/Ester Ratio | Liver/Body Weight % Change |
|---|---|---|---|---|---|---|
| Cholesterol Fed Controls | 4 | 34.1 ± 13.6 | 10.1 ± 5.9 | 17.3 ± 3.4 | 1.35 ± 0.33 | 0 |
| Cholesterol Fed CPD 16 100 mg/kg/day | 5 | 20.5 ± 3.4 | 3.1 ± 1.2 | 20.7 ± 2.7 | 2.23 ± 0.27 | +8 |
| Cholesterol Fed CPD 16 200 mg/kg/day | 5 | 25.9 ± 2.9 | 3.9 ± 1.4 | 26.3 ± 3.1 | 2.24 ± 0.46 | +12 |

TABLE X

AORTA CHOLESTEROL CLEARING ACTIVITY OF COMPOUND 16 IN CHOLESTEROL PRE-FED RABBITS TREATED FOR 4 MONTHS

|  | Aortic Cholesterol | | | | Aortic Phospholipids | | |
|---|---|---|---|---|---|---|---|
|  | Total mg/Aorta | Arch mg/g | Thoracic mg/g | Free/Ester Ratio | Total mg/Aorta | Arch mg/g | Thoracic mg/g |
| Cholesterol Fed Controls n = 4 | 36.5 ± 8.7 | 30.9 ± 2.2 | 20.4 ± 5.2 | 1.1 ± 0.2 | 13.4 ± 1.5 | 7.1 ± 1.8 | 9.0 ± 1.7 |
| Cholesterol Fed CPD 16 Treated 100 mg/kg/day n = 5 | 20.8 ± 6.5 | 17.9 ± 2.9* | 10.6 ± 2.8 | 0.5 ± 0.1* | 6.5 ± 1.6** | 4.6 ± 1.4 | 4.5 ± 1.5* |
| Cholesterol Fed CPD 16 Treated 200 mg/kg/day n = 5 | 18.3 ± 6.7 | 22.8 ± 3.4 | 11.0 ± 4.2 | 0.4 ± 0.1** | 7.9 ± 1.8* | 5.9 ± 1.3 | 4.9 ± 1.9 |

*p < 0.05
**p < 0.01

TABLE XI

DECREASED ATHEROMATEOUS SURFACE INVOLVEMENT AND DECREASED INTIMA THICKENING OF AORTAS IN CHOLESTEROL PRE-FED RABBITS TREATED WITH COMPOUND 16 FOR 4 MONTHS

|  | Surface Involved in Atheromateous Plaques % | | | Arterial Wall Thickness Units in Area | | | |
|---|---|---|---|---|---|---|---|
|  | | | | Arch | | Thoracic | |
|  | Total Aorta | Arch | Thoracic | Intima | Intima/Media Ratio | Intima | Intima/Media Ratio |
| Controls n = 3 | 81 ± 10 | 96 ± 4 | 69 ± 14 | 62.83 ± 0.64 | 1.36 | 10.54 ± 0.15 | 0.41 |
| CPD 16 Treated 100 mg/kg/day n = 4 | 68 ± 12 | 88 ± 9 | 50 ± 15 | 41.82 ± 0.93* | 0.79* | 7.66 ± 0.12* | 0.23* |
| CPD 16 Treated 200 mg/kg/day n = 4 | 53 ± 10 | 79 ± 5 | 30 ± 14 | 32.37 ± 0.37* | 0.68* | 1.99 ± 0.05* | 0.07* |

*p < 0.01

TABLE XII

CARDIOVASCULAR AND LIPOPROTEIN CHANGES PRODUCED BY ONE DOSE OF COMPOUND 16 TO A CYNOMOLGUS MONKEY

|  | −30 min. | 0 | +1h. | +2h. | +3h. | +5h. | +6h. |
|---|---|---|---|---|---|---|---|
| $\alpha/\beta$ cholesterol ratio | 0.66 | 0.68 | 0.71 | 0.82 | 0.83 | 0.89 | 0.92 |
| Blood pressure mmHg | 115 | — | 65 | 70 | 100 | 95 | 105 |
| Heart Rate (beat/min.) | 225 | 210 | 195 | — | 195 | 210 | 210 |

250 mg/kg p.o.

TABLE XIII

INDUCED LIPOPROTEIN CHANGES IN NORMAL CYNOMOLGUS MONKEY TREATED WITH COMPOUND 16

| Time | n | Total Cholesterol mg/100 ml | alpha Cholesterol mg/100 ml | beta Cholesterol mg/100 ml | alpha/beta Cholesterol Ratio |
|---|---|---|---|---|---|
| Pretest 1 13 Days | 9 | 102 ± 6 | 39 ± 3 | 61 ± 5 | 0.66 |
| Pretest 2 6 Days | 9 | 106 ± 3 | 40 ± 5 | 69 ± 5 | 0.54 |
| SR-202 Treated 45 Days | 7 | 99 ± 8 | 54 ± 5* | 46 ± 4** | 1.17** |
| SR-202 Treated 60 Days | 7 | 85 ± 7** | 46 ± 4 | 41 ± 5** | 1.09** |

Dose: 25 mg/kg/day for 45 days 50 mg/kg/day for last 15 days
*p < 0.05
**p < 0.01

Thus the treatment of normal monkeys with compound 16 at essentially therapeutic dosage levels over longer time periods similarly induces an augmentation in HDL (α-cholesterol) and a significant increase in $\alpha/\beta$ ratio. In addition blood urea levels were noted to be significantly lower in the treated animals compared to controls.

In order to further elucidate the mechanism of the previously observed hypotensive activity, the renin-angiotensin system was also monitored in these animals at the same time. At 60 days the treated animals had a renin activity of 0.3±0.1 ng $A_I$/ml/h compared to 5.9±0.9 ng $A_I$/ml/h for control animals (Table XIV). The results show that compound 16 produces a highly significant and almost complete inhibition of renin in male and female monkeys during 60 days of treatment even at low-dosage levels. However at this dosage concentration the inhibition appeared to be time dependent.

Since renin and angiotensin are physiologically associated with maintaining blood pressure, it is quite apparent that the hypotensive effect of compounds of this type are principally related to renin inhibition. Due to the fact that approximately 70% of all patients with essential hypertension have elevated levels of renin further implicates these compounds as being useful in treating hypertension. (Case, D. B. et al American J. of Medicine 61,790–796, 1976, Case D. B. et al N. Engl. J. of Medicine 296,641–646, 1977).

These diphosphonate compounds have a broad therapeutic application in the field of cardiovascular diseases since it is well known that there is a strong correlation between the development of coronary heart diseases, atherosclerosis and hypertension. (Strong J. P. et al The Pathogenesis of Atherosclerosis, ed. Wissler and Geer Williams and Wilkins Baltimore 1972 p. 24.)

Simultaneous cholesterol feeding and treatment with compound 16 to male and female Cynomolgus monkeys over 60 days likewise, demonstrated the interspecies consistancy of compound 16 to increase HDL-C values and the $\alpha/\beta$ ratios (Table XIV). Again the renin values were essentially completely inhibited (20 fold inhibition) during the simultaneous cholesterol-compound 16 treatment.

Five human patients were treated over several days with either 5 mg/kg or 10 mg/kg of compound 16 (Table XV). Similarly as was seen in rat and monkey (even at these lower dose levels) compound 16 demonstrates that there is a significant increase in $HDL_3$-cholesterol. Of equal importance was the finding that the free/total cholesterol ratio in the respective isolated lipoprotein fractions is significantly elevated. It is generally recognized that an increase in free cholesterol ratio is indicative of an increased clearing or turnover of the lipoprotein cholesterol (Schwartz, C. C. Biochem. Biophys. Acta 663:143-162, 1981).

In conclusion, the consistency of the data in rodent, primate and man in relationship to the known protective role of HDL-C and importance of an elevated $\alpha/\beta$ ratio, gives to these diphosphonate compounds a significant potential in treating cardiovascular disease states associated with atherosclerosis and hypertension.

TABLE XIV

CHANGES INDUCED BY COMPOUND 16 IN CYNOMOLGUS MONKEYS FED SIMULTANEOUSLY A HIGH CHOLESTEROL DIET DURING 60 DAYS

| Days on High Cholesterol Diet | | Renin Activity ng $A_I$/ml/h | Plasma Lipoproteins | |
|---|---|---|---|---|
| | | | $\alpha/\beta$ Chol. ratio | HDL Chol. mg/100 ml |
| 30 Days | controls n = 5 | 10.9 ± 1.9 | 0.15 ± 0.08 | 29 ± 4 |
| | treated n = 7 | 0.8 ± 0.5* | 0.22 ± 0.05 | 49 ± 4* |
| 60 Days | controls n = 5 | 23.5 ± 0.4 | 0.08 ± 0.01 | 16 ± 1 |
| | treated n = 7 | 1.1 ± 0.2* | 0.22 ± 0.05* | 39 ± 6* |

*Statistically significant
p < 0.05
Dose: 25 mg d.i.d. per day

Safe and effective amounts of phosphonate compound are prepared in sufficient amounts to produce a desirable effect at a reasonable benefit/risk ratio attendant with any medical treatment. Within the scope of acceptable and sound medical judgment, the dosage of phosphonate compound will vary with the particular condition being treated, the severity of the condition, the duration of the treatment, and the specific phosphonate compound employed.

The phosphonates are prepared as pharmaceutically acceptable products which include all ingredients used in the compositions employed and are suitable for use in contact with the tissues of humans and animals without undue toxicity, irritation, allergic response commensurate with a reasonable benefit/risk ratio.

Preparation of the pharmaceutical compositions according to the present invention for oral unit dosage forms can be a mixture with a solid vehicle containing lactose, saccharose, sorbitol, mannitol, starch, amylopectine, cellulose derivative, and/or gelatine which can be prepared with the lubricants such as magnesium stearate, calcium stearate, forms of "carbowax" and/or polyethylene glycol. It can be preferable in some cases to use a capsule, and the ingredients can then consist of a mixture containing concentrated sugar, arabic gum, talc, and/or titan bioxide.

For example capsules were prepared using between 10 to 40% of pharmaceutical grade lactose with compound 16 to have final concentrations of 10, 20, 50, 100, or 250 mg per capsule.

In some cases particular phosphonates can be mixed in buffer solution, corn oil, olive oil, glycerol, commercial fillers, and administered in closed hard gelatine capsule, as drops, or syrup forms.

In addition, the phosphonates can be fabricated with "Imhausen H" to produce suitable suppositories.

For example, compounds 16 to 23 were compressed in tablet form with magnesium stearate 10% and amidon 25% to obtain a final concentration of about 100 to 300 mg active agent. In addition compounds of formula (I) were made up in solution of sterile water, drinking water or corn oil at concentrations between about 2 mg/ml and 100 mg/ml.

What is claimed is:

1. A pharmaceutical composition having anti-atherosclerotic activity by reducing tissue lipids and favorably altering plasma lipids, which comprises as active ingredient an antiatherosclerotically effective amount of a diphosphonate ester compound of the formula

wherein X is H or OH; m is zero or 1, R is $CH_3$ or $C_2H_5$ but when m is zero and X is OH then R is only $CH_3$; and A is selected from the group consisting of

TABLE XV

| | EFFECT OF COMPOUND 16 ON LIPOPROTEINS FROM 5 TREATED HUMAN PATIENTS | | | | | | | |
|---|---|---|---|---|---|---|---|---|
| | VLDL | | LDL | | $HDL_2$ | | $HDL_3$ | |
| n = 5 | Cholesterol mmol/l | Free/Total Cholesterol ratio | Cholesterol mmol/l | Free/Total Cholesterol ratio | Cholesterol mmol/l | Free/Total Cholesterol ratio | Cholesterol mmol/l | Free/Total Cholesterol ratio |
| Pre-test | 0.34 ± 0.06 | 0.416 ± 0.021 | 2.92 ± 0.30 | 0.297 ± 0.005 | 0.95 ± 0.10 | 0.186 ± 0.011 | 0.53 ± 0.05 | 0.217 ± 0.043 |
| CPD 16 5 mg/kg | 0.20 ± 0.03 | 0.472 ± 0.019 (+14%) | 3.05 ± 0.26 | 0.304 ± 0.005 | 0.82 ± 0.13 | 0.231 ± 0.027 (+24%) | 0.72 ± 0.09* (+36%) | 0.242 ± 0.018 (+12%) |
| CPD 16 10 mg/kg | 0.26 ± 0.03 | 0.519 ± 0.031* (+25%) | 2.86 ± 0.23 | 0.303 ± 0.002 | 0.87 ± 0.07 | 0.221 ± 0.003* (+19%) | 0.60 ± 0.02 (+13%) | 0.285 ± 0.044 (+32%) |

*Statistically significant (Paired t-Test) p < 0.05

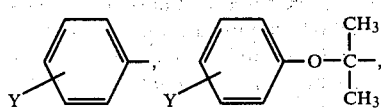 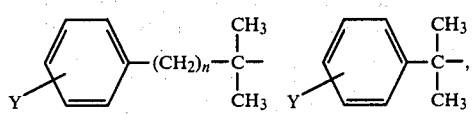

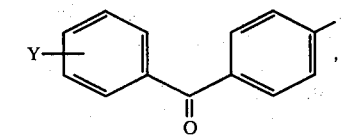

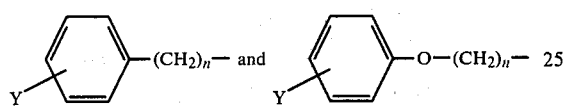

where n is an integer from 1 to 6 and Y is H, CH₃, OCH₃ or halogen, A being other than

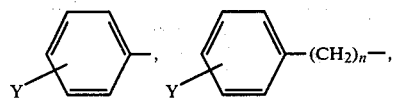

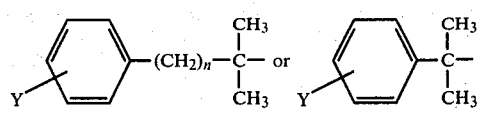

when m is zero, and a pharmaceutically acceptable excipient.

2. A composition according to claim 1, in which said compound is of the formula

where R and A are as defined in claim 1.

3. A composition according to claim 1, in which said compound is of the formula

where R and A are as defined in claim 1.

4. A composition according to claim 1, in which said compound is of the formula

where R and A are as defined in claim 1.

5. A composition according to claim 1 in which Y is H or a chlorine atom in para position.

6. A composition according to claim 1, in which said compound is tetramethyl 2,2-dimethyl 2-(p-chlorophenoxy) ethane 1-hydroxy-1,1-diphosphonate.

7. A composition according to claim 1, in which said compound is tetramethyl 1-[4(4'-chlorobenzoyl)-phenyl]-methane 1-hydroxy 1,1-diphosphonate.

8. A composition according to claim 1, in which said compound is dimethyl α(dimethoxyphosphinyl)p-chlorobenzyl phosphate.

9. A composition according to claim 1, in which said compound is dimethyl α(dimethoxyphosphinyl)p-fluorobenzyl phosphate.

10. A composition according to claim 1, in which said compound is dimethyl [1(dimethoxyphosphinyl) 2,2-dimethyl 2-phenyl]-ethyl phosphate.

11. A composition according to claim 1, in which said compound is dimethyl [1(dimethoxyphosphinyl) 2,2-dimethyl 2(p-chlorophenyl)] ethyl phosphate.

12. A composition according to claim 1, in which said compound is dimethyl [α-(dimethoxyphosphinyl) 4-(4'-chlorobenzoyl)] benzyl phosphate.

* * * * *